United States Patent [19]

Ito et al.

[11] Patent Number: 4,850,366
[45] Date of Patent: Jul. 25, 1989

[54] ULTRASONIC DIAGNOSIS APPARATUS FOR DISPLAYING SPEED OR CORRELATION BETWEEN SPEED AND SPEED DISPERSION BY COLOR CHANGE

[75] Inventors: Yukio Ito; Yutaka Sato; Shinji Kishimoto; Satoshi Tamano, all of Kashiwa, Japan

[73] Assignee: Hitachi Medical Corp., Tokyo, Japan

[21] Appl. No.: 165,406

[22] Filed: Feb. 26, 1988

Related U.S. Application Data

[63] Continuation of Ser. No. 806,394, Dec. 9, 1985, abandoned.

[30] Foreign Application Priority Data

Dec. 12, 1984 [JP] Japan ................................ 59-263199

[51] Int. Cl.$^4$ .............................................. A61B 10/00
[52] U.S. Cl. ............................ 128/661.08; 73/861.25
[58] Field of Search ..................... 128/660, 661, 663; 73/861.25, 861.06

[56] References Cited

U.S. PATENT DOCUMENTS

| | | | |
|---|---|---|---|
| 3,909,771 | 9/1975 | Pickering et al. ...................... | 73/620 |
| 3,986,160 | 10/1976 | Turner .................................... | 73/617 |
| 4,387,597 | 6/1983 | Brandestini ........................... | 128/660 |
| 4,562,540 | 12/1985 | Devaney ............................... | 128/660 |
| 4,573,477 | 3/1986 | Namekawa et al. ............... | 73/861.25 |

Primary Examiner—Maryann Lastova
Attorney, Agent, or Firm—Antonelli, Terry & Wands

[57] ABSTRACT

An ultrasonic diagnosis apparatus comprises an ultrasonic probe for transmitting an ultrasonic pulse beam toward an internal moving member of a living body at a constant recurrence frequency, a converter for mixing the received high-frequency signal with a set of complex reference signals having a frequency n times as high as the recurrence frequency of the transmitted ultrasonic pulse beam and having a complex relation therebetween, thereby converting the high-frequency signal into complex signals, a speed operating circuit for computing the speed of the moving part on the basis of the complex signals, a speed deviation operating circuit for computing the deviation of the speed computed by the speed operator, and a display unit for displaying, by a color change, at least one of the speed, the speed dispersion, the speed and the speed deviation, and the correlation between the speed and the speed deviation. The display unit may display the reflected ultrasonic wave intensity by a luminance and may display the correlation between the reflected ultrasonic wave intensity and the speed and/or the speed deviation by a color change.

5 Claims, 8 Drawing Sheets

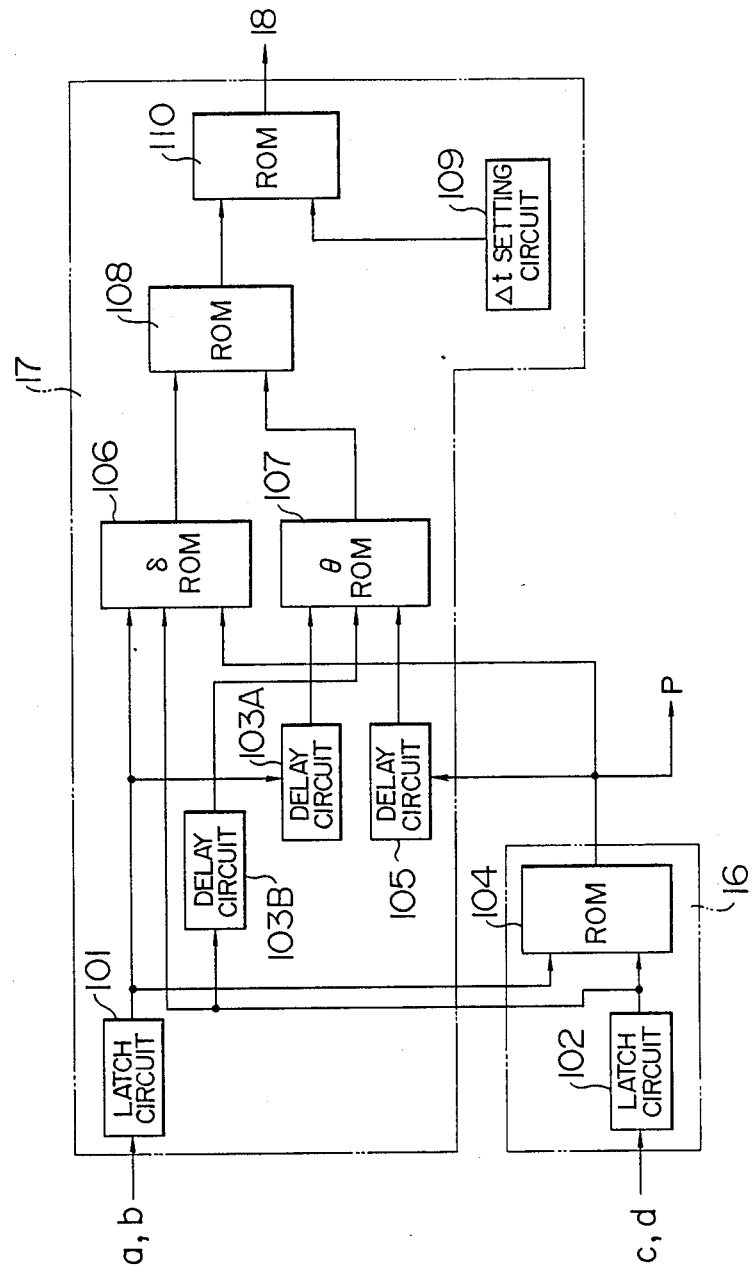
F I G. 7

ULTRASONIC DIAGNOSIS APPARATUS FOR DISPLAYING SPEED OR CORRELATION BETWEEN SPEED AND SPEED DISPERSION BY COLOR CHANGE

This application is a continuation of application Ser. No. 806,394 filed Dec. 9, 1985, now abandoned.

BACKGROUND OF THE INVENTION

This invention relates to the art of detecting and displaying the state of an internal moving medium of a living body, and more particularly to a novel technique which is effectively applicable to an ultrasonic diagnosis apparatus used for measurement and display of the moving speed (referred to hereinafter simply as speed) of an internal moving medium of a living body, the dispersion of the moving speed (referred to hereinafter simply as speed dispersion), the intensity of an ultrasonic beam reflected from the internal moving medium of the living body, etc.

An ultrasonic pulse-Doppler method has been put into practical use for the measurement of the speed of an internal moving part of a living body, for example, a visceral organ such as the heart or a fluid such as blood or humor in a circulatory organ.

A prior art, ultrasonic diagnosis apparatus utilizing the ultrasonic pulse-Doppler method displays three kinds of information of such an internal moving medium, that is, the speed, moving direction and speed dispersion as video or picture information. In the case of actual display, the speed of the moving medium is displayed by relative luminance, and the moving direction of the moving part is displayed by a color selected depending on the direction. Further, for the display of the speed dispersion, a color used for displaying the speed dispersion is mixed with a pre-selected color indicative of the speed in a proportion corresponding to the rate of speed dispersion, thereby displaying the speed dispersion by a color change.

However, in the case of the prior art displaying means, recording of a picture displaying the speed by the luminance is dependent upon the recording characteristics of a recording system. Therefore, the reproducibility of the luminance of a picture signal has not been satisfactory, and it has been nearly impossible to read the speed on the displayed picture or photograph.

Further, in the case of the prior art displaying means, information of the intensity of the ultrasonic wave reflected from the internal moving medium of the living body (the reflected power spectrum) has not been displayed. The reflected ultrasonic wave intensity referred to above corresponds to the flow rate of, for example, blood when the internal moving medium of the living body is blood flow, and is thus a parameter indicative of the rate of motion of the moving medium.

In an apparatus such as, a pulse-Doppler blood flow meter, which is now widely employed in this field and which resorts to the method of high-speed Fourier transformation for displaying the motion of an internal moving medium of a living body, the intensity of an ultrasonic beam reflected from the moving medium is displayed by luminance. Accordingly, displaying the speed by luminance has led to the problem that the speed displayed by the luminance cannot be distinguished from the reflected ultrasonic beam intensity which is also displayed by the luminance in the prior art system, resulting in a possible change of the basis of diagnosis.

SUMMARY OF THE INVENTION

It is an object of the present invention to provide an ultrasonic diagnosis apparatus in which at least one of the speed, the speed dispersion, the speed and speed dispersion, the correlation between the reflected ultrasonic wave intensity and the speed, the correlation between the speed and the speed dispersion, and the correlation between the reflected ultrasonic wave intensity and the speed and speed dispersion can be displayed by a color change. The display of the speed dispersion is made in the case where the moving medium is a fluid in a living body such as blood or humor.

Another object of the present invention is to provide an ultrasonic diagnosis apparatus in which the reflected ultrasonic wave intensity is displayed by luminance, and at least one of the speed, the speed dispersion, the speed and speed dispersion, the correlation between the reflected ultrasonic wave intensity and the speed, the correlation between the speed and the speed dispersion, and the correlation between the reflected ultrasonic wave intensity and the speed and speed dispersion can be displayed by a color change.

The present invention is directed to an ultrasonic diagnosis apparatus in which an ultrasonic pulse beam is transmitted toward an internal moving medium of a living body at a constant recurrence frequency, and the reflected wave from the internal moving medium of the living body is received and displayed after being processed. According to the present invention, the received high-frequency signal is mixed with a set of complex reference signals having a frequency n times (n: an integer) as high as the recurrence frequency of the transmitted ultrasonic pulse beam and having a complex relation therebetween thereby converting the received high-frequency signal into complex signals. The moving speed of the internal moving medium of the moving body is computed on the basis of the complex signals, and the dispersion of the speed of the moving medium is then computed. According to one aspect of the present invention, at least one of the speed, the speed dispersion, the speed and speed dispersion, and the correlation between the speed and the speed dispersion is displayed by a color change, thereby providing sufficient amounts of information required for diagnosis. According to another aspect of the present invention, the reflected ultrasonic wave intensity computed on the basis of the complex signals is displayed by luminance, and at least one of the speed, the speed dispersion, the speed and speed dispersion, the correlation between the speed and the speed dispersion, the correlation between the reflected ultrasonic wave intensity and the speed, and the correlation between the reflected ultrasonic wave intensity and the speed and speed dispersion is displayed by a color change, thereby providing more information required for diagnosis.

BRIEF DESCRIPTION OF THE DRAWINGS

FIG. 7 is a block diagram showing the detailed structure of one form of the reflected ultrasonic wave intensity operating circuit and one form of the speed operating circuit shown in FIG. 2.

DESCRIPTION OF THE PREFERRED EMBODIMENTS

Figure 1:
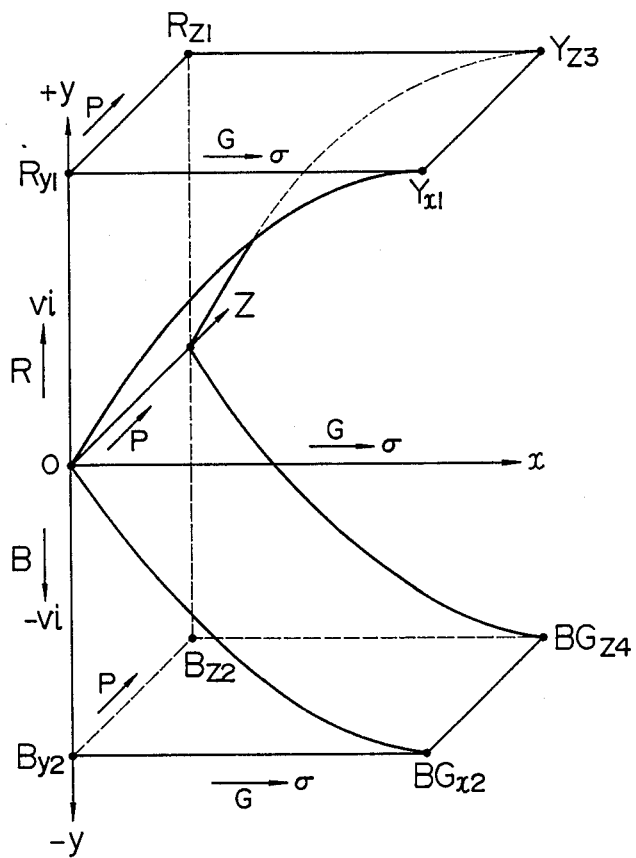
FIG. 1 is a diagrammatic view showing how the speed of an internal moving medium of a living body, the speed dispersion, the reflected ultrasonic wave intensity and their correlations are displayed by colors according to the principle of a preferred embodiment of the ultrasonic diagnosis apparatus of the present invention.

A preferred embodiment of the present invention showing an application of the present invention to an ultrasonic diagnosis apparatus adapted to display information of an internal moving medium of a living body according to the method of high-speed Fourier transformation, will be described in detail with reference to the accompanying drawings. In the drawings, the same reference numerals are used to designate the same functional parts.

First, the principle of the manner of display according to the present invention will be described.

The outline of the principle of the manner of display is such that the information of an internal moving medium of a living body is displayed by a changing luminance corresponding to the intensity of an ultrasonic beam reflected from the internal moving medium so as to attain compatibility with a prior art manner of display of such information according to the method of high-speed Fourier transformation.

Figure 11:
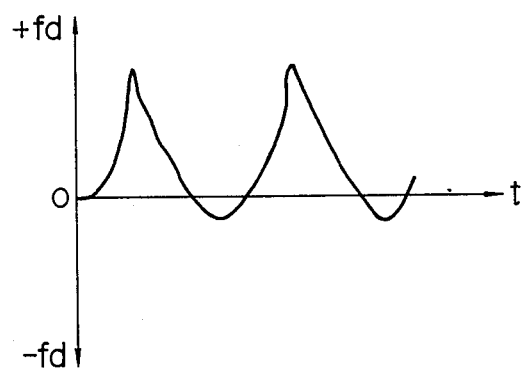
FIGS. 11 and 12 show characteristic curves for illustrating problems encountered with a prior art ultrasonic diagnosis apparatus.

The prior art manner of displaying the information of an internal moving medium of a living body comprises detecting the motion of the internal moving medium by the known ultrasonic pulse-Doppler method, subjecting the result of detection to high-speed Fourier transformation, and displaying the time-dependent change of the speed of the internal moving medium. According to the prior art displaying method, the moving direction and speed of the internal moving medium of the living body at the point of measurement are displayed in such a manner that as shown in FIG. 11, the direction and speed $f_d$ (the amount of Doppler shift at the point of measurement) of the approaching motion and the receding motion are indicated in an analog fashion on the vertical axis. The horizontal axis represents the time-dependent change (t) of the moving direction and speed of internal moving part, and the concentration of the pattern indicative of the motion of the internal moving medium is proportional to the intensity of the ultrasonic wave reflected from the internal moving medium under motion. However, in the case of a two-dimensional color display, the amount of Doppler shift at the point of measurement, that is, the moving direction and speed of the internal moving member at the point of measurement cannot be displayed by plotting their values on the time axis as described above. Therefore, the moving direction and speed of the internal moving medium are indicated by a changing color and a changing luminance respectively on the sectional (tomographic) image taken at the point of measurement.

Figure 12:
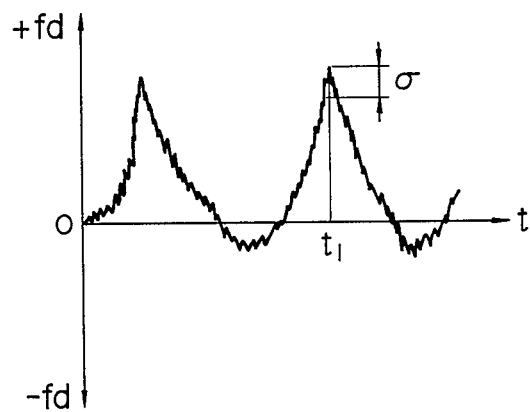

Further, in the case of a color display according to the prior art method of high-speed Fourier transformation, a changing color must be used for the display of the speed dispersion $\sigma$ for the same reason, when the speed deviation $\sigma$ is observed at the point of measurement as shown in FIG. 12 also.

In FIGS. 11 and 12, $f_d$ represents the amount of Doppler shift, and t represents the time. The affixed symbols "+" and "−" indicate the approaching and receding directions respectively.

In a preferred embodiment of the present invention, a color indicative of the speed dispersion $\sigma$ is mixed with colors indicative of the moving speed and direction of the internal moving medium in a proportion corresponding to the amount of speed dispersion, so that the moving speed, moving direction, speed dispersion and their correlations at individual points of measurement can be indicated by colors.

The principle of color display employed in the embodiment of the present invention will be described in detail with reference to FIG. 1.

In FIG. 1, the symbol x designates an axis representing the speed dispersion $\sigma$, and this speed dispersion $\sigma$ is displayed by, for example, green. The symbol y designates an axis representing the speed of an internal moving medium of a living body. The symbol "+" indicates the approaching direction and the approaching speed $v_i$ is displayed by, for example, red. The symbol "−" indicates the receding direction and the receding speed $v_i$ is displayed by, for example, blue. The symbol z designates an axis representing the intensity P of the ultrasonic wave reflected from the internal moving part, and this reflected ultrasonic wave intensity P is displayed by luminance.

The symbols $Y_{x1}$, $BG_{x2}$, $R_{y1}$, $B_{y2}$, and O designate dark yellow, dark deep bluish green, dark deep red, dark deep blue, and the boundary between light red and light blue, respectively.

The symbols $R_{z1}$, $B_{z2}$, $Y_{z3}$, and $BG_{z4}$ designate bright deep red, bright deep blue, bright yellow, and bright deep bluish green, respectively.

An ultrasonic pulse beam is transmitted toward an internal moving medium of a living body at a constant recurrence frequency, and the reflected ultrasonic wave from the internal moving part of the living body is received. The received high-frequency signal is mixed with a set of complex reference signals having a frequency n times (n: an integer) as high as the recurrence frequency of the transmitted ultrasonic pulse beam and having a complex relation therebetween thereby converting the received high-frequency signal into complex signals. On the basis of these complex signals, the speed and speed dispersion of the internal moving medium of the living body and the intensity of the ultrasonic wave reflected from the internal moving medium are computed by associated operating circuit. Depending on the computed amounts of these information, the speed, speed dispersion and reflected wave intensity are displayed by the combination of colors and luminance as shown in FIG. 1.

Describing in further detail, the distance from the origin on the y-axis corresponds to the speed of motion of, for example, blood flow, and, at a point distance from the origin, the speed of blood flow is high, while, at a point close to the origin, the speed of the blood flow is low. The approaching motion is displayed by, for example, red. The approaching motion at a high speed is indicated by the deep red color $R_{y1}$ or $R_{z1}$ (for example, magenta), and the approaching motion at a low speed is indicated by a light red color (for example, pink). In this manner, a changing red color is displayed depending on the speed of the approaching motion.

On the other hand, the receding motion is displayed by, for example, as blue. The receding motion at a high speed is indicated by the deep blue color $B_{y2}$ or $B_{z2}$ (for example, ultramarine), and the receding motion at a low speed is indicated by a light blue color (for example, sky blue). In this manner, a changing blue color is displayed depending on the speed of the receding motion.

Further, the speed dispersion $\sigma$ is displayed by mixing a green color, changing depending on the value of speed dispersion, with the red or blue color.

As described above, the color used for display is determined depending on the speed or the speed and speed dispersion according to the manner of display in the embodiment of the present invention, and the luminance is not changed depending on the speed and/or speed dispersion.

According to the present invention, the luminance of the color signal determined by the speed and/or speed dispersion is changed depending on the intensity of the ultrasonic wave reflected from the internal moving medium of the living body.

An example of the above manner of color display will now be described.

As described above, the luminance of a color signal determined by the moving direction, speed and speed dispersion of an internal moving medium of a living body is changed depending on the intensity of the ultrasonic wave reflected from the internal moving medium, for displaying the intensity of the reflected ultrasonic wave. Suppose, for example, that a display used for the displaying purpose is capable of displaying 64 tones of each of red (referred to hereinafter as R), green (referred to hereinafter as G) and blue (referred to hereinafter as B). With such a display, R, G and B of 8 tones each are used to display the speed, and the distribution ratio of the tones of R, G and B is determined depending on the detected speed. For the color display of the speed dispersion, G is further mixed, and the distribution ratio of the tones of R, G and B is determined depending on the moving direction, speed and speed dispersion to determine the color for displaying the speed dispersion. The intensity of the reflected ultrasonic wave is displayed by one of 8 grades combined with the distribution ratio of R, G and B described above. For example, the tone selected from the 8 tones is multiplied by the tones of R, G and B determined previously to adjust the luminance of the detected intensity of the reflected ultrasonic wave without changing the distribution ratio of R, G and B.

Figure 2:
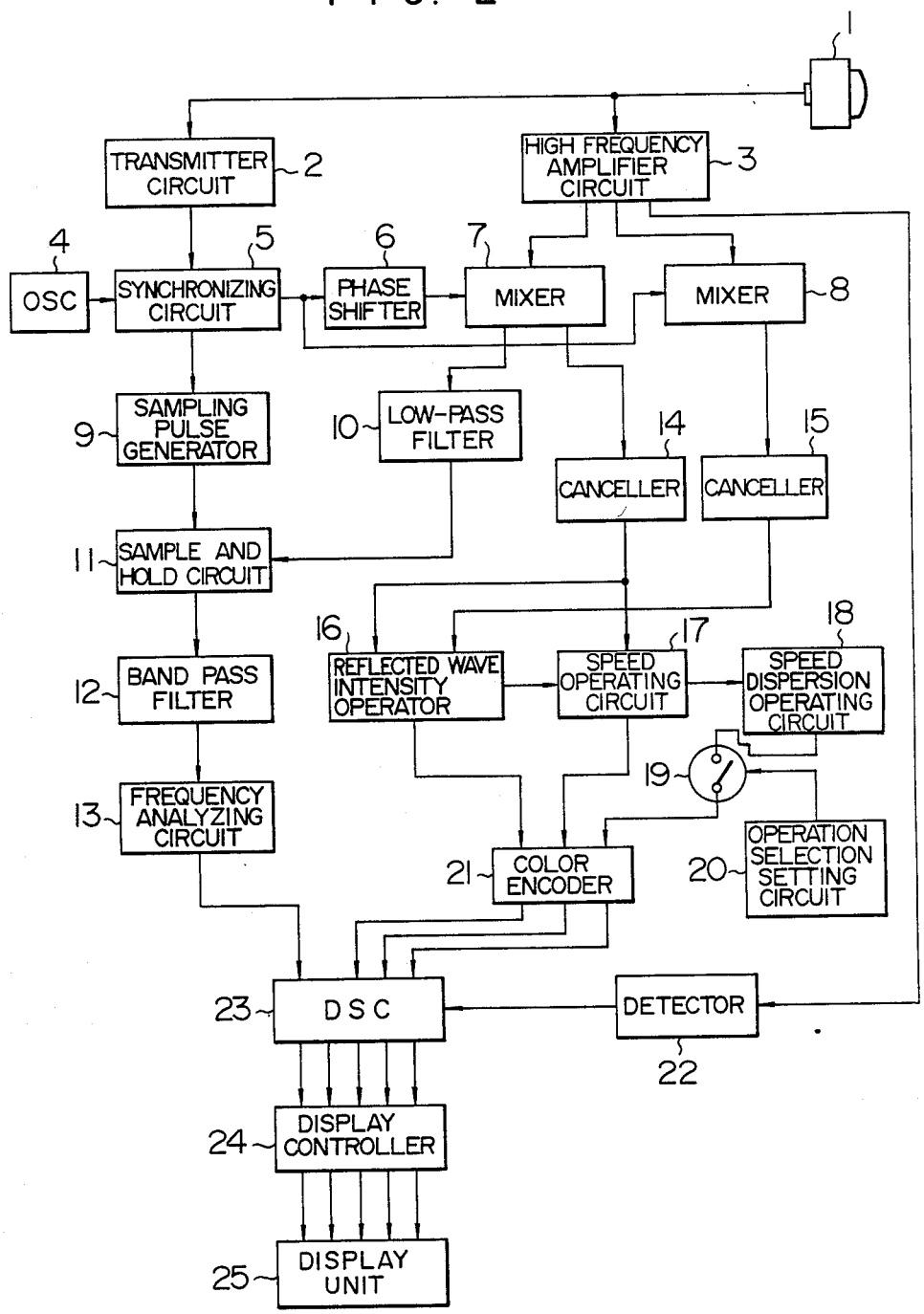
FIG. 2 is a block diagram showing the general structure of the preferred embodiment of the ultrasonic diagnosis apparatus of the present invention.

FIGS. 2 to 10 illustrate the structure and operation of the preferred embodiment of the ultrasonic diagnosis apparatus of the present invention based on the principle of display described above. FIG. 2 is a block diagram showing schematically the general structure of the ultrasonic diagnosis apparatus.

Referring to FIG. 2, an ultrasonic beam transmitted toward an internal moving medium of a living body from an ultrasonic probe 1 is produced by a transmitter circuit 2. Pulses of the transmitted ultrasonic beam are reflected from the internal moving medium of the living body to be received by the ultrasonic probe 1. The received high frequency signal including internal information of the living body is amplified by a high-frequency amplifier circuit 3. A crystal oscillator 4 generates a high-frequency synchronizing signal. This high-frequency synchronizing signal is converted by a synchronizing circuit 5 into a reference signal having a frequency corresponding to the recurrence frequency of the ultrasonic pulses transmitted from the ultrasonic probe 1. The phase of the reference signal generated from the synchronizing circuit 5 is shifted by 90° by a phase shifter 6. The 90°-phase shifted reference signal from the phase shifter 6 is mixed with the amplified received signal in a first mixer 7 which acts to provide information of the moving direction of the moving medium which is, for example, blood flow. On the other hand, the reference signal from the synchronizing circuit 5 is directly mixed with the amplified received signal in a second mixer 8.

A first canceller 14 and a second canceller 15 extract only Doppler components having information of the internal moving medium of the living body from the output signals of the first and second mixers 7 and 8 respectively. A reflected ultrasonic-wave intensity operating circuit 16 computes the intensity of the ultrasonic wave reflected from the internal moving medium of the living body (the intensity of each signal including the extracted Doppler component). A speed operating circuit 17 computes the speed of the internal moving medium of the living body on the basis of the canceller output signals representing the extracted Doppler components. A speed deviation operating circuit 18 computes the value of speed dispersion on the basis of the value of the speed computed by the speed operating circuit 17. The received signal is thus converted by the speed operating circuit 17 and speed dispersion operating circuit 18 into a signal indicative of the speed and a signal indicative of the speed dispersion. An operation selector switch 19 is provided to determine whether the speed only is to be computed or whether both the speed and the speed dispersion are to be computed. This operation selector switch 19 is changed over under control of an operation selection setting circuit 20. The operation selector switch 19 may be disposed between the speed operating circuit 17 and the speed dispersion operator 18. A color encoder 21 generates output signals determining the proportions of the combination of the three primary colors R, G and B depending on the information of the speed (the direction and speed), speed dispersion and reflected ultrasonic wave intensity. A detector 22 detects the received signal including the internal information of the living body amplified by the high-frequency amplifier circuit 3 so as to extract a sectional image signal of the internal moving part of the living body. This extracted sectional image signal is written in a digital scan converter (abbreviated hereinafter as a DSC) 23.

The high-frequency component of the output signal of the first mixer 7 is removed by a low-pass filter 10, and the output signal of the low-pass filter 10 is applied to a sample and hole circuit 11. In order to extract a one-dimensional Doppler shift component from the output signal of the low-pass filter 10 in a usual manner, a gate pulse signal produced by a sampling pulse generator 9 is applied to the sample and hold circuit 11 thereby extracting the signal representing the Doppler shift of the internal moving medium of the living body. After being smoothed by a band-pass filter 12, the Doppler shift signal is applied to a frequency analyzing circuit 13 there the one-dimensional Doppler shift signal is extracted as by high-speed Fourier transformation. This one-dimensional Doppler shift signal is also written in the DSC 23.

The signals indicative of the internal information of the living body, written in the DSC 23, are converted into a video signal in the DSC 23 and read out as a television signal to be displayed on a display unit 25 such as a CRT monitor or a television monitor through a display controller 24.

Among the internal information of the living body, the speed and speed dispersion are computed according to arithmetic formulas or expressions described later.

In order to compute the speed and speed dispersion, of an internal moving member at a certain predetermined depth it is necessary to detect amounts of Doppler shift occurring in a plurality of ultrasonic waves reflected from the predetermined depth. For conveniences of description, it is supposed herein that the number of received signals is two.

Figure 3:
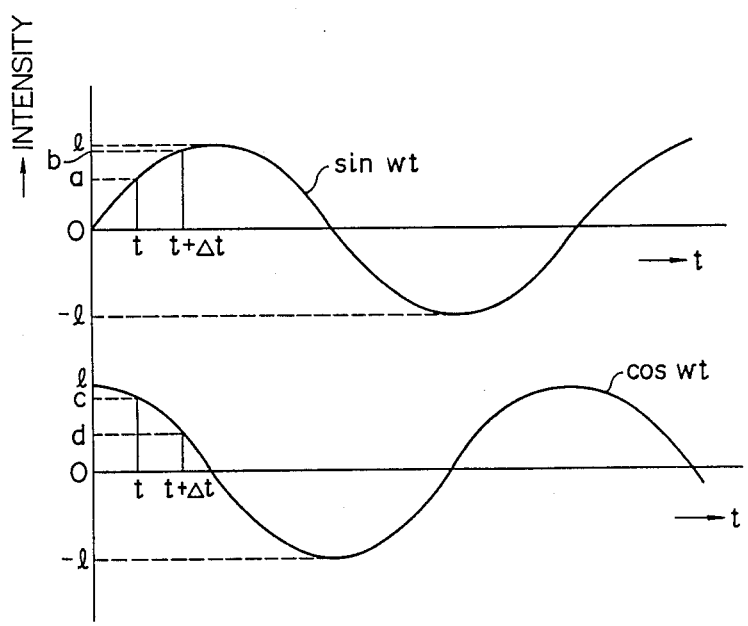
FIGS. 3 to 6 illustrate how the speed and speed dispersion are computed in the embodiment of the present invention.

The ultrasonic beam is transmitted from the ultrasonic probe 1 toward an internal moving member of a living body at a time interval of $\Delta t$, and ultrasonic waves reflected from the internal moving member of the living body are received by the ultrasonic probe 1. When a time-dependent change of each reflection point is taken into consideration, the intensity at the reflection point of the Doppler signal extracted from each of the received signals is represented by the value, at a certain time, of a periodic function representing a certain intensity and having a period of Doppler shift. In order to detect the intensity represented by the periodic function and resulting from the Doppler shift (that is, the kinetic momentum of the internal moving member of the living body), the combination of the phase shifter 6 and the mixers 7, 8 produces signals having a phase difference of 90° on the basis of the received signals. The intensities a, b, c and d of Doppler shift, at a certain depth, of the four signals in total are given by phases at times t (t+$\Delta t$) as shown in FIG. 3.

More precisely, the intensities a and c, at time t, of the functions having the period (frequency) $f_d$ of Doppler shift and having the phase difference of 90° therebetween are expressed respectively as follows:

$$a = l \sin 2\pi f_d t \qquad (1)$$

$$c = l \cos 2\pi f_d t \qquad (2)$$

where l is the absolute value of the intensity of the signal received at time t.

Similarly, the intensities b and d at time (t+$\Delta t$) are expressed respectively as follows:

$$b = l \sin 2\pi f_d(t + \Delta t) \qquad (3)$$

$$d = l \cos 2\pi f_d(t + \Delta t) \qquad (4)$$

On the basis of these expressions (1) to (4), the absolute intensities $l_t$ and $l_{(t+\Delta t)}$ of the functions at times t and (t+$\Delta t$) are expressed respectively as follows:

$$l_t = (a^2 + c^2)^{\frac{1}{2}} \qquad (5)$$

$$l_{(t+\Delta t)} = (b^2 + d^2)^{\frac{1}{2}} \qquad (6)$$

These absolute intensities $l_t$ and $l_{(t+\Delta t)}$ are proportional to the flow rate of a fluid, for example, blood in the living body.

How to compute the moving speed of the fluid in the living body will next be described.

Figure 4:
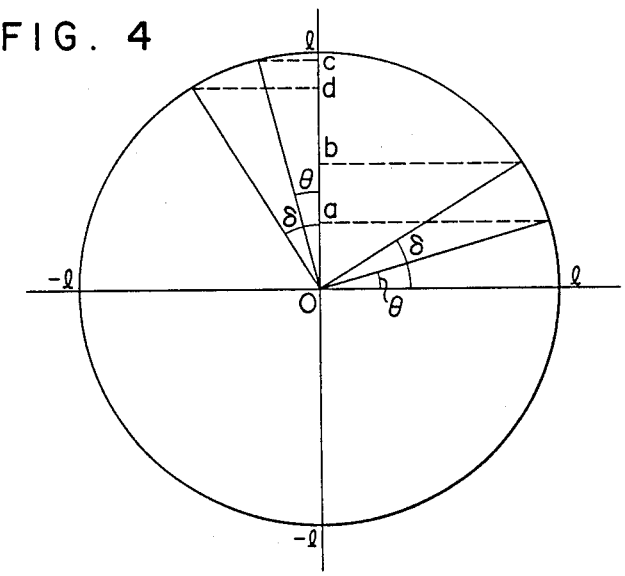

FIG. 4 illustrates that, at times t and (t+$\Delta t$), the Doppler waves have respective angular displacements $\theta$ and $\delta$ which are expressed as follows:

$$\theta = \sin^{-1}\left(\frac{a}{l_t}\right) \qquad (7)$$

$$\delta = \sin^{-1}\left(\frac{b}{l_{(t + \Delta t)}}\right) \qquad (8)$$

It is to be noted that the values of $\theta$ and $\delta$ determined by the expressions (7) and (8) lie within the ranges of $-90° < \theta < 90°$ and $-90° < \delta < 90°$ respectively. Therefore, in order to determine the values of $\theta$ and $\delta$ so that they lie within the ranges of $$0° < \theta < 360°, 0° < \delta < 360°$$

Figure 5:
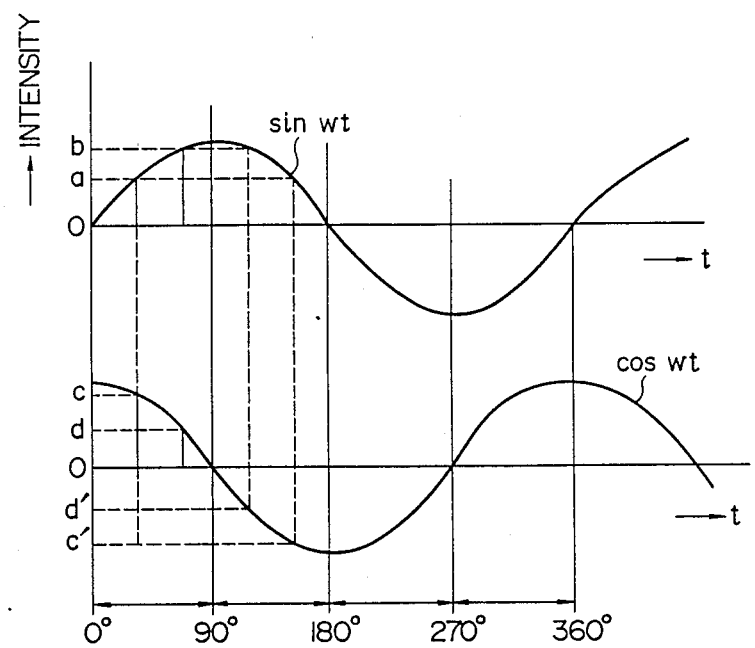
Figure 6:
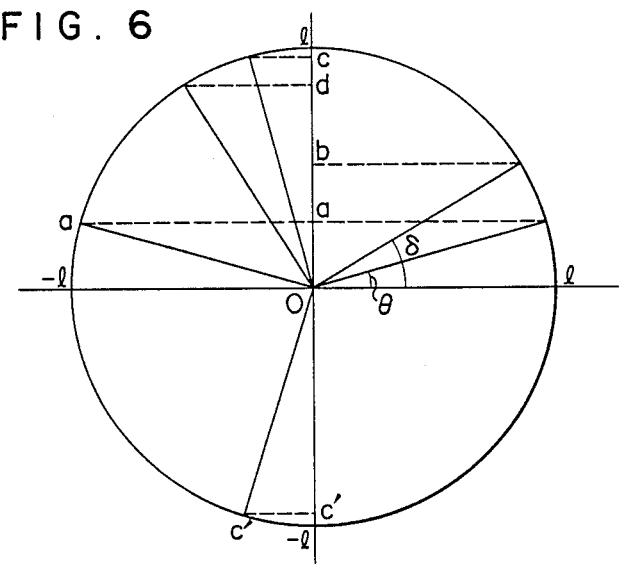

The value of $\theta$ is computed on the basis of a (l sin $2\pi f_d t$), c (l cos $2\pi f_d t$) and c' [l cos ($\pi - 2\pi f_d t$)], as shown in FIGS. 5 and 6. Similarly, the value of $\delta$ is computed on the basis of b=[l sin $2\pi f_d$(t−$\Delta t$)] and d=[l cos $2\pi f_d$(t−$\Delta t$)].

That is, depending on whether the sine and cosine components of the signals having the phase difference of 90° are positive or negative, the value of x in $\sin^{-1} x$ lies is various ranges as shown in the following Table I:

TABLE I

| sin component | cos component | Range of x |
| --- | --- | --- |
| Positive | Positive | 0° < X < 90° |
| Positive | Negative | 90° < X < 180° |
| Negative | Negative | 180° < X < 270° |
| Negative | Positive | 270° < X < 360° |

On the basis of Table I, the values of $\theta$ and $\delta$ given by the expressions (7) and (8) respectively are computed. The displacement angle $\Delta\theta$ of $\theta$ in the minute length of time of change $\Delta t$ is computed according to the following expression (10) on the basis of the expressions (7) and (8):

$$\Delta\theta = \theta - \delta \qquad (10)$$

The angular velocity $\omega$ is expressed as follows:

$$\omega = \Delta\theta/\Delta t \qquad (11)$$
$$= (\delta - \theta)/\Delta t$$

From the above expression (11), the frequency $f_d$ of the Doppler shift is expressed as follows:

$$f_d = 2\pi \cdot \omega$$
$$= 2\pi \cdot (\delta - \theta)/\Delta t$$

Since this Doppler shift frequency $f_d$ is proportional to the speed of the fluid flow in the living body, the moving direction of the fluid and the speed of the fluid flow in the living body can be computed on the basis of the Doppler shift frequency $f_d$.

The reflected ultrasonic-wave intensity operating circuit 16 and the speed operating circuit 17 shown in FIG. 2 compute the reflected ultrasonic wave intensity and the speed respectively according to the relevant expressions. FIG. 7 shows the detailed structure of one form of the reflected ultrasonic-wave intensity operating circuit 16 and that of one form of the speed operating circuit 17.

Referring to FIG. 7, the values of the sine component, [a given by the expression (1) and b given by the expression (3)], of the signals received at times t and $(t+\Delta t)$ are sequentially supplied to and temporarily latched in that order in a first latch circuit 101. Similarly, the values of the cosine component, [c given by the expression (2) and d given by the expression (4)], of the signals received at the times t and $(t+\Delta t)$ are sequentially supplied to and temporarily latched in that order in a second latch circuit 102.

A first delay circuit 103A is connected to the output of the first latch circuit 101 to provide the value of the sine component of the signal extracted from the preceding ultrasonic beam received from the same depth, that is, the value of a given by the expression (1). A second delay circuit 103B is connected to the output of the second latch circuit 102 to provide the value of the cosine component of the signal extracted from the preceding ultrasonic beam received from the same depth, that is, the value used for computation of $\sin^{-1}$ shown in Table I. An operator 104, which is in the form of a ROM (a read-only memory), has a table for computing the absolute value, [the value of $l_t$ given by the expression (5)], of the intensity of the received signal on the basis of the value of the sine component [a given by the expression (1)] and the value of the cosine component [c given by the expression (2)]. A third delay circuit 105 is connected to the output of the ROM 104 to provide the absolute value [the value of $l_{(t+\Delta t)}$ given by the expression (6)] of the intensity of the signal extracted from the preceding ultrasonic beam received from the same depth. A second ROM 106 has a table for computing the value of the angle $\delta$ according to the expression (8) and Table I on the basis of the data outputs of the latch circuits 101, 102 and ROM 104. A third ROM 107 has a table for computing the value of the angle $\theta$ according to the expression (7) and Table I on the basis of the data outputs of the delay circuits 103A, 103B and 105. A fourth ROM 108 has a table for computing the value of the displacement angle $\Delta\theta$ according to the expression (10) on the basis of the data outputs of the ROM's 106 and 107.

A $\Delta t$ setting circuit 109 sets the time interval $\Delta t$ of the transmission of the ultrasonic beam from the ultrasonic probe 1. A fifth ROM 110 has a table for computing the value of the angular velocity $\omega$ given by the expression (11) on the basis of the data output of the ROM 108 and the value of the setting of the time interval $\Delta t$ of ultrasonic beam transmission.

The operation of the speed operating circuit 17 having such a construction will be described with reference to FIG. 7.

The data b of the sine component of the signal extracted from the reflected wave received at time $(t+\Delta t)$ is supplied from the canceller 14 shown in FIG. 2 to the first latch circuit 101, and the data d of the cosine component of the signal extracted from the received wave is suppled from the canceller 15 to the second latch circuit 102. From the latch circuits 101 and 102, the data b and d of the sine and cosine components of the signal are supplied to the first ROM 104, and, from this ROM 104, the absolute value $l_t$ of the intensity of the received ultrasonic beam is supplied to the second ROM 106. Since the data b and d of the sine and cosine components of the received signal have been supplied from the first and second latch circuits 101 and 102 respectively to the second ROM 106 to be used for the computation of the value of the angle $\delta$ according to the expression (8), the computed value of the angle $\delta$ at time $(t+\Delta t)$ is supplied from the second ROM 106 to the fourth ROM 108. The data output of the first ROM 104 is also supplied to the third delay circuit 105 to be delayed by the setting of the time interval $\Delta t$ of ultrasonic beam transmission. At the same time, the absolute value $l_t$ of the intensity of the signal extracted from the preceding ultrasonic beam received is supplied to the third ROM 107. Since the data a and c of the since and cosine components of the signal extracted from the preceding ultrasonic beam received have been supplied to this ROM 107 from the first and second delay circuits 103A and 103B respectively to be used for the computation of the value of the angle $\theta$ according to the expression (7), the computed value of the angle $\theta$ at time t is supplied from the third ROM 107 to the fourth ROM 108 to be used for the computation of the displacement angle $\Delta\theta$ according to the expression (10). This computed value of $\Delta\theta$ is supplied to the fifth ROM 110 together with the value of $\Delta t$ supplied from the $\Delta t$ setting circuit 109 to be used for the computation of the angular velocity $\omega$ according to the expression (11), and the computed value of $\omega$ is supplied to the speed dispersion operating circuit 18 and DSC 23.

Figure 8:
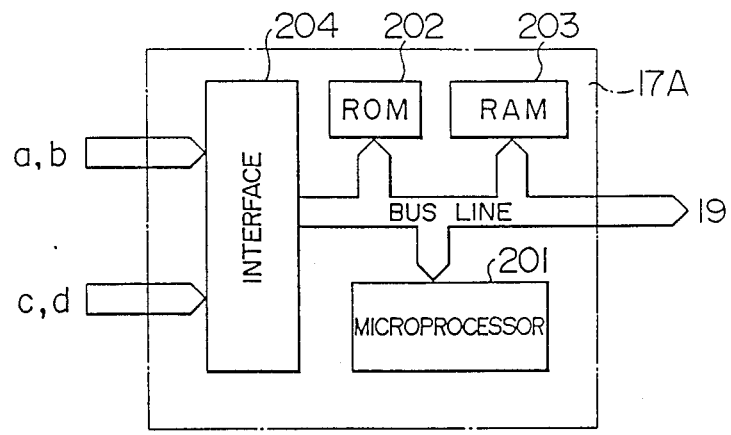
FIG. 8 is a block diagram showing the detailed structure of another form of the reflected ultrasonic beam intensity operating circuit and another form of the speed operating circuit shown in FIG. 2.

Another form of the speed operator 17 is shown in FIG. 8. Referring to FIG. 8, the speed operator 16A includes a microprocessor 201, a ROM 202, a RAM (a random access memory) 203 and an interface 204 connected together by a bus line. In this speed operator 17A, the expressions (1) to (11) are computed according to a software program.

The detailed structure of one form of the speed dispersion operating circuit 18 shown in FIG. 2 will be described with reference to FIG. 9.

The computation of the speed dispersion $\sigma$ carried out in this speed dispersion operator 17 is expressed as follows:

$$\sigma^2 = \frac{1}{n} \sum_{i=1}^{n} (v_i - \overline{N})^2 \text{ or } \sigma = \sqrt{\frac{1}{n} \sum_{i=1}^{n} (v_i - \overline{N})^2} \quad (12)$$

$$\overline{N} = \frac{1}{n} \sum_{i=1}^{n} v_i \quad (13)$$

where $v_i$ [i: 1 to n (an integer)] is the moving speed computed by the speed operator 16, and $\overline{N}$ is the average speed.

Figure 9:
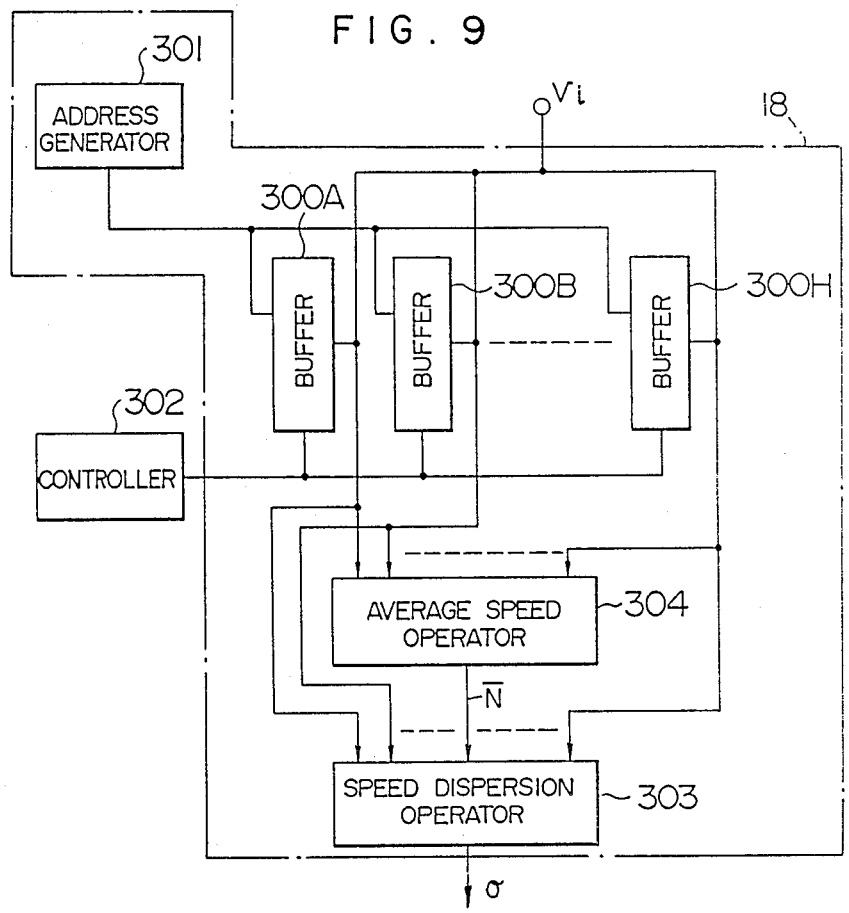
FIG. 9 is a block diagram showing the detailed structure of one form of the speed dispersion operating circuit shown in FIG. 2.

Referring to FIG. 9, buffers 300A to 300H store data of the moving speed $v_i$. These buffers 300A to 300H, for example, each have a capacity enough to store speed data extracted from the reflected wave of one ultrasonic beam.

An address generator 301 generates addresses of the buffers 300A to 300H. These buffers 300A to 300H are selected under control of a controller 302 which is included in a control apparatus controlling the entire system. An ordinary operator 303 executes the computation of the speed dispersion $\sigma$ according to the expression (12). Another ordinary operator 304 computes the average speed $\overline{N}$ according to the expression (13).

Figure 10:
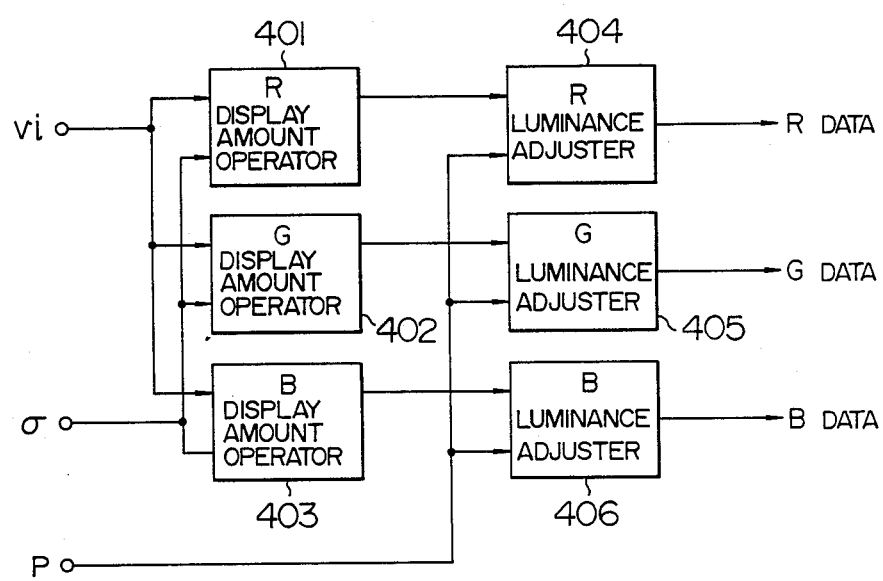
FIG. 10 is a block diagram showing the detailed structure of one form of the color encoder shown in FIG. 2.

FIG. 10 shows the detailed structure of one form of the color encoder 21 shown in FIG. 2.

Referring to FIG. 10, an R display amount operator 401, a G display amount operator 402 and a B display amount operator 403 compute the values of mixing proportions of the three primary colors R, G and B depending on the computed speed $v_i$ and speed dispersion $\sigma$ to be displayed. The display color is produced by mixing the three primary colors R, G and B according to the computed values. The R display amount operator 401 computes the amount of the R component in the displayed color, the G display amount operator 402 computes the amount of the G component, and the B display amount operator 403 computes the amount of the B component.

An R luminance adjuster 404, a G luminance adjuster 405 and a B luminance adjuster 406 are connected to the R, G and B display amount operators 401, 402 and 403 respectively so that the luminance of the display color provided by mixing R, G and B according to the computed proportions is proportional to the reflected ultrasonic wave intensity P.

The R, G and B display amount operators 401, 402 and 403 are in the form of ROM's storing tabulated results of computation previously done on the basis of the aforementioned principle as, for example, shown in Tables II, III and IV respectively.

The R, G and B luminance adjusters 404, 405 and 406 adjust the luminance according to, for example, Tables V, VI and VII respectively in which the lumiance to be displayed is divided into 64 grades which have been previously experimentally determined. For the sake of convenience, the speed and speed deviation are represented by digital values of 5 bits and 3 bits respectively, and quantitized equivalents are shown in Tables II to VII.

TABLE II

R display amount operation table

| Speed dispersion / Speed | 0 | 1 | 2 | 3 | 4 | 5 | 6 | 7 |
|---|---|---|---|---|---|---|---|---|
| $-8 \sim -7$ | 8 | 8 | 8 | 8 | 8 | 8 | 8 | 8 |
| $-6 \sim -5$ | 7 | 7 | 7 | 7 | 7 | 7 | 7 | 7 |
| $-4 \sim -3$ | 6 | 6 | 6 | 6 | 6 | 6 | 6 | 6 |
| $-2 \sim -1$ | 5 | 5 | 5 | 5 | 5 | 5 | 5 | 5 |
| 0 | 0 | 0 | 0 | 0 | 0 | 0 | 0 | 0 |
| $2 \sim 1$ | 4 | 4 | 4 | 4 | 4 | 4 | 4 | 4 |
| $4 \sim 3$ | 3 | 3 | 3 | 3 | 3 | 3 | 3 | 3 |
| $6 \sim 5$ | 2 | 2 | 2 | 2 | 2 | 2 | 2 | 2 |
| $8 \sim 7$ | 1 | 1 | 1 | 1 | 1 | 1 | 1 | 1 |

TABLE III

G display amount operation table

| Speed dispersion / Speed | 0 | 1 | 2 | 3 | 4 | 5 | 6 | 7 |
|---|---|---|---|---|---|---|---|---|
| $-8 \sim -7$ | 0 | 1 | 2 | 3 | 4 | 5 | 6 | 7 |
| $-6 \sim -5$ | 0 | 1 | 2 | 3 | 4 | 5 | 6 | 7 |
| $-4 \sim -3$ | 0 | 1 | 2 | 3 | 4 | 5 | 6 | 7 |
| $-2 \sim -1$ | 0 | 1 | 2 | 3 | 4 | 5 | 6 | 7 |
| 0 | 0 | 0 | 0 | 0 | 0 | 0 | 0 | 0 |
| $2 \sim 1$ | 0 | 1 | 2 | 3 | 4 | 5 | 6 | 7 |
| $4 \sim 3$ | 0 | 1 | 2 | 3 | 4 | 5 | 6 | 7 |
| $6 \sim 5$ | 0 | 1 | 2 | 3 | 4 | 5 | 6 | 7 |
| $8 \sim 7$ | 0 | 1 | 2 | 3 | 4 | 5 | 6 | 7 |

TABLE IV

B display amount operation table

| Speed dispersion / Speed | 0 | 1 | 2 | 3 | 4 | 5 | 6 | 7 |
|---|---|---|---|---|---|---|---|---|
| $-8 \sim -7$ | 1 | 1 | 1 | 1 | 1 | 1 | 1 | 1 |
| $-6 \sim -5$ | 2 | 2 | 2 | 2 | 2 | 2 | 2 | 2 |
| $-4 \sim -3$ | 3 | 3 | 3 | 3 | 3 | 3 | 3 | 3 |
| $-2 \sim -1$ | 4 | 4 | 4 | 4 | 4 | 4 | 4 | 4 |
| 0 | 0 | 0 | 0 | 0 | 0 | 0 | 0 | 0 |
| $2 \sim 1$ | 5 | 5 | 5 | 5 | 5 | 5 | 5 | 5 |
| $4 \sim 3$ | 6 | 6 | 6 | 6 | 6 | 6 | 6 | 6 |
| $6 \sim 5$ | 7 | 7 | 7 | 7 | 7 | 7 | 7 | 7 |
| $8 \sim 7$ | 8 | 8 | 8 | 8 | 8 | 8 | 8 | 8 |

TABLE V

R luminance adjusting table

| Reflected wave / Amount of R | 0 | 1 | 2 | 3 | 4 | 5 | 6 | 7 |
|---|---|---|---|---|---|---|---|---|
| 0 | 0 | 0 | 0 | 0 | 0 | 0 | 0 | 0 |
| 1 | 0 | 1 | 2 | 3 | 4 | 5 | 6 | 7 |
| 2 | 0 | 2 | 4 | 6 | 8 | 10 | 12 | 14 |
| 3 | 0 | 3 | 6 | 9 | 12 | 15 | 18 | 21 |
| 4 | 0 | 4 | 8 | 12 | 16 | 20 | 24 | 28 |
| 5 | 0 | 5 | 10 | 15 | 20 | 25 | 30 | 35 |
| 6 | 0 | 6 | 12 | 18 | 24 | 30 | 36 | 42 |
| 7 | 0 | 7 | 14 | 21 | 28 | 35 | 42 | 49 |
| 8 | 0 | 8 | 16 | 24 | 32 | 40 | 48 | 56 |

TABLE VI

G luminance adjusting table

| Reflected wave intensity / Amount of G | 0 | 1 | 2 | 3 | 4 | 5 | 6 | 7 |
|---|---|---|---|---|---|---|---|---|
| 0 | 0 | 0 | 0 | 0 | 0 | 0 | 0 | 0 |
| 1 | 0 | 1 | 2 | 3 | 4 | 5 | 6 | 7 |
| 2 | 0 | 2 | 4 | 6 | 8 | 10 | 12 | 14 |
| 3 | 0 | 3 | 6 | 9 | 12 | 15 | 18 | 21 |
| 4 | 0 | 4 | 8 | 12 | 16 | 20 | 24 | 28 |
| 5 | 0 | 5 | 10 | 15 | 20 | 25 | 30 | 35 |
| 6 | 0 | 6 | 12 | 18 | 24 | 30 | 36 | 42 |
| 7 | 0 | 7 | 14 | 21 | 28 | 35 | 42 | 49 |

TABLE VII

B luminance adjusting table

| Reflected wave intensity / Amount of B | 0 | 1 | 2 | 3 | 4 | 5 | 6 | 7 |
|---|---|---|---|---|---|---|---|---|
| 0 | 0 | 0 | 0 | 0 | 0 | 0 | 0 | 0 |
| 1 | 0 | 1 | 2 | 3 | 4 | 5 | 6 | 7 |
| 2 | 0 | 2 | 4 | 6 | 8 | 10 | 12 | 14 |
| 3 | 0 | 3 | 6 | 9 | 12 | 15 | 18 | 21 |
| 4 | 0 | 4 | 8 | 12 | 16 | 20 | 24 | 28 |
| 5 | 0 | 5 | 10 | 15 | 20 | 25 | 30 | 35 |
| 6 | 0 | 6 | 12 | 18 | 24 | 30 | 36 | 42 |
| 7 | 0 | 7 | 14 | 21 | 28 | 35 | 42 | 49 |
| 8 | 0 | 8 | 16 | 24 | 32 | 40 | 48 | 56 |

The operation of the color encoder 21 employed in the embodiment of the present invention will be described with reference to FIG. 10.

When the data of the speed $v_i$ and that of the speed dispersion $\sigma$ are supplied to the R, G and B display amount operators 401, 402 and 403, the R display amount operator 401 generates an output signal indicative of the amount of the R component among those of the three primary colors R, G and B corresponding to the speed $v_i$ and speed dispersion $\sigma$ to be displayed, the G display amount operator 402 generates an output signal indicative of the amount of the G component, and the B display amount operator 403 generates an output signal indicative of the amount of the B component. These output signals are applied to the R, G and B luminance adjusters 404, 405 and 406 respectively, together with the data of the luminance corresponding to the reflected ultrasonic wave intensity P. Therefore, the luminance indicative of the reflected ultrasonic wave intensity P is added to the color corresponding to the speed $v_i$ and speed dispersion $\sigma$ to be displayed.

In the embodiment of the present invention, the input data of the speed $v_i$, speed dispersion $\sigma$ and reflected ultrasonic wave intensity P shown in Tables II, III and IV and Tables V, VI and VII are those of 5 bits, 3 bits and 3 bits respectively. However, the capacities of these tables may be easily increased so that the speed $v_i$, speed dispersion $\sigma$ and reflected ultrasonic wave intensity P are represented by data of more bits, for example, k bits, l bits and m bits respectively.

The operation of the entire ultrasonic diagnosis apparatus will now be described with reference to FIG. 2.

The ultrasonic pulse beam transmitted from the ultrasonic probe 1 toward an internal moving part of a living body is produced by the transmitter circuit 2. The transmitted ultrasonic pulse beam is reflected by the internal moving part of the living body and received by the ultrasonic probe 1. The received high-frequency signal including the internal information of the living body is amplified by the high-frequency amplifier circuit 3. The stable high-frequency signal generated from the crystal oscillator 4 is converted by the synchronizing circuit 5 into a reference signal having a frequency corresponding to or n times (n: an integer) as high as the recurrence frequency of the transmitted ultrasonic pulse beam, and this reference signal is applied to the second mixer 8 to be mixed with the received and amplified, high-frequency signal applied to the mixer 8. Further, the reference signal is also applied to the phase shifter 6 to be phase-shifted by 90°, and the output signal of the phase shifter 6 is applied to the first mixer 7 to be mixed with the high-frequency signal received by the ultrasonic probe 1 and amplified by the high-frequency amplifier circuit 3, for providing the information of the moving direction of the internal moving medium of the living body. The output signals of the mixers 7 and 8 are applied to the respective cancellers 14 and 15 which extract only the Doppler components carrying the kinetic information of the internal moving medium of the living body. The canceller output signals including the extracted Doppler components are applied to the reflected ultrasonic-wave intensity operator 16 which computes the value of the reflected ultrasonic wave intensity P according to the aforementioned procedure on the basis of the input signals including the extracted Doppler components. The data of the computed, reflected ultrasonic wave intensity P is supplied to the color encoder 21 and to the speed operating circuit 17.

The signals including the Doppler components are also applied from the canceller 14 to the speed operating circuit 17, and, on the basis of the input signals including the Doppler components and the input data of the reflected ultrasonic wave intensity P, the speed operator 17 computes the speed $v_i$ according to the aforementioned procedure. The speed dispersion operating circuit 18 computes the speed dispersion $\sigma$ according to the aforementioned procedure. The data of the computed speed $v_i$ and that of the computed speed dispersion $\sigma$ are supplied to the color encoder 21. In the color encoder 21, the luminance data indicative of the reflected ultrasonic wave intensity P is added to the color data indicative of the R, G and B components used for color display of the data of the speed $v_i$ and speed dispersion $\sigma$, and the resultant R, G and B display data appear from the color encoder 21 to be stored in the DSC 23.

Whether the computation to find the speed $v_i$ only is to be carried out or the computation to find both the speed $v_i$ and the speed dispersion $\sigma$ is to be carried out, as determined by the operation selection setting circuit 20, and the operation selector switch 19 is opened or closed.

Also, the living-body signal received by the ultrasonic probe 1 and amplified by the amplifier circuit 3 is applied directly to the detector 22 which detects the signal representing the sectional image of the internal moving medium of the living body, and the data output of the detector 22 is stored in the DSC 23.

The low-pass filter 10 removes the high-frequency component of the output signal of the first mixer 7. The gate pulse signal generated from the sampling pulse generator 9 is applied to the sample and hold circuit 11 so that a one-dimensional Doppler shift component can be extracted in a usual manner from the output signal of the low-pass filter 10. The signal indicative of the Doppler shift of the internal moving medium of the living body is extracted in the sample and hold circuit 11, and the output signal of the sample and hold circuit 11 is applied, after being smoothed by the band-pass filter 12, to the frequency analyzing circuit 13 which extracts the one-dimensional Doppler shift signal from the input signal. This extracted Doppler shift signal is also stored in the DSC 23.

The various data stored in the DSC 23 are supplied through the display controller 24 to the display unit 25 which displays a color picture having a color and a luminance corresponding to the values of the speed $v_i$, speed dispersion $\sigma$ and reflected ultrasonic wave intensity P. The display unit 25 can also display the sectional image of the internal moving medium and/or the Doppler wave.

Tables tabulating the results of all the computations may be stored in the ROM's of the reflected ultrasonic-wave intensity operating circuit 16 and speed operating circuit 17 so that the computing speed can be increased. Also, the speed dispersion operator 18 may include ROM's having tables tabulating the results of all the computations so that the computation of the average speed $\overline{N}$ on the basis of the speed information stored in the buffers can be computed at a higher speed.

It will be seen from the above description that the embodiment of the present invention illustrated in FIGS. 1 to 10 provides the following advantages:

(1) Since the reflected ultrasonic wave intensity P is displayed by the luminance, noise that may be contained in the Doppler shift signal indicative of motion of an internal moving medium of a living body due to a step of signal control such as gain control can be removed from the display. That is, the lower limit of the Doppler shift signal in a desired range of measurement can be set as required. Therefore, the Doppler shift signal indicative of, for example, a large quantity of blood flow can be selectively displayed when so desired.

(2) Any change in the speed of the internal moving medium of the living body at each of individual sampling points is displayed by a color change. Therefore, the difference between the speeds of the internal moving medium at each of the individual sampling points can be observed.

(3) The speed and speed dispersion of the internal moving medium of the living body are displayed by a two-dimensional color change. Therefore, the correlation between the speed and the speed dispersion of the internal moving medium of the living body can be immediately observed.

(4) The luminance which changes depending on the intensity of the ultrasonic wave reflected from the internal moving medium of the living body is superposed on a color display displaying the speed and speed dispersion of the internal moving medium by the two-dimensional color change. Therefore, the correlation between the reflected ultrasonic wave intensity and the speed and speed deviation of the internal moving medium of the living body can be immediately observed.

(5) When two-dimensional color displays displaying the factors described in (1) to (4) are photographed, the difference between the speeds of the internal moving medium of the living body at each of individual sampling points, the correlation between the speed and the speed dispersion of the internal moving medium at each of the individual sampling points, etc. can be recorded. Therefore, the difference between the speeds of the internal moving member at each of the individual sampling points, the correlation between the speed and the speed dispersion of the internal moving medium at each of the indivudual sampling points, etc. can be observed later when so required.

(6) The difference between the speeds of the internal moving medium of the living body at each of individual sampling points is displayed by a color display which is less dependent on the characteristics of a recording system than the prior art luminance display. Therefore, the reproducibility of the speed difference display can be improved.

(7) By virtue of the advantages (1) to (6) described above, effective data required for the diagnosis can be provided.

(8) The speed and speed dispersion operating circuits 17 and 18 employing ROM's only for the computation of the speed and speed dispersion are incorporated to dispense with the use of the prior art autocorrelator. Therefore, the size of the apparatus can be reduced, and the cost of the apparatus can also be reduced.

(9) Since the speed and speed dispersion operating circuits 17 and 18 employing ROM's for the computation of the speed and speed dispersion are used, the computation speed can be increased.

(10) By virtue of the provision of the operation selection setting circuit 20, the speed or both the speed and the speed dispersion can be selectively computed for a color display. Therefore, only the data required for the diagnosis can be quickly provided.

(11) By virtue of the advantages (1) to (4) described above, the intensity of the ultrasonic wave reflected from the internal moving medium of the living body scanned by the ultrasonic beam, the speed, and both the speed and the speed dispersion of the internal moving medium at each of individual depths can be measured and computed at a high speed. Therefore, more information required for the diagnosis of an internal organ of a living body can be provided to improve the accuracy of diagnosis.

Although a preferred embodiment of the present invention has been described in detail by way of example, it is apparent that the present invention is in no way limited to such a specific embodiment, and various changes and modifications may be made therein without departing the subject matter of the present invention.

It will be understood from the foregoing detailed description that the present invention provides the following advantages:

(1) Noise that may be contained in the Doppler shift signal indicative of motion of an internal moving medium of a living body due to the display of the reflected ultrasonic wave intensity by the luminance can be removed from the color display. Thus, the lower limit of the Doppler shift signal in a desired range of measurement can be determined as required. Therefore, the Doppler shift signal indicative of, for example, a large quantity of blood flow can be selectively displayed when so required.

(2) Any change in the speed of the internal moving medium of the living body at each of individual sampling points is displayed by a color change. Therefore, the difference between the speeds of the internal moving part at each of the individual sampling points can be observed.

(3) The speed and speed dispersion of the internal moving part are displayed by a two-dimensional color change. Therefore, the correlation between the speed and the speed dispersion of the internal moving part of the living body can be immediately observed.

(4) The luminance which changes depending on the intensity of the ultrasonic wave reflected from the internal moving medium of the living body is superposed on a color display displaying the speed and speed dispersion of the internal moving medium by the two-dimensional color change. Therefore, the correlation between the reflected ultrasonic wave intensity and the speed and speed dispersion of the internal moving medium of the living body can be immediately observed.

We claim:

1. An ultrasonic diagnosis apparatus comprising:

an ultrasonic probe for transmitting an ultrasonic pulse beam toward a moving medium in a living body at a predetermined time interval $\Delta t$ defining a constant recurrence frequency and for receiving a reflected signal from a portion of the moving medium at any given depth in the living body;

converting means for mixing the received signal with a set of complex reference signals having a frequency n times (n: an integer) as high as the recurrence frequency of the transmitted ultrasonic pulse beam and having a complex relation therebetween, thereby converting the received signal into complex signals including a sine component signal and a cosine component signal;

first operating means for computing the moving speed of the moving medium at said given depth in the living body on the basis of said complex signals, said first operating means using values a and b of said sine component signal at time t and time $(t+\Delta t)$ and values c and d of said cosine component signal said times t and $(t+\Delta t)$ to compute intensities $l_t$ and $l_{(t+\Delta t)}$ represented by $$l_t = (a^2 + c^2)^{\frac{1}{2}}$$

and $$l_{(t+\Delta t)} = (b^2 + d^2)^{\frac{1}{2}},$$

using the computed values of intensities $l_t$ and $l_{(t+\Delta t)}$ to compute angular displacement $\theta$ and $\delta$ represented by $$\theta = \frac{a}{\sin^{-1} l_t}$$

and $$\delta = \frac{b}{\sin^{-1} l_{(t+\Delta t)}},$$

and using the computed values of angular displacements $\theta$ and $\delta$ and the value of said predetermined time interval $\Delta t$ to compute a Doppler shift frequency $f_d$ represented by $$f_d = 2\pi \cdot (\delta - \theta)/\Delta t,$$

the moving speed of the moving medium at said given depth in the living body being determined from the computed value of Doppler shift frequency $f_d$;

second operating means for computing the dispersion $\sigma$ of the moving speed computed by said first operating means when said moving medium is a fluid in the living body, said moving speed dispersion $\sigma$ being represented by $$\sigma = \sqrt{\frac{1}{n} \sum_{i=1}^{n} (v_i - \overline{N})^2},$$

$v_i$ being the values of the moving speed at said given depth in the living body computed by said first operating means and $\overline{N}$ being an average speed determined by $$\overline{N} = \frac{1}{n} \sum_{i=1}^{n} v_i,$$

n being an integer;

operation selecting means associated with said second operating means for selecting whether the computation of the moving speed by said first operating means is to be executed or both the computation of the moving speed by said first operation means and the moving speed dispersion by said second operating means are to be executed; and display means for displaying, by a color change, at least one of the moving speed computed by said first operating means, and the correlation between the moving speed and the moving speed dispersion computed by said second operating means.

2. An ultrasonic diagnosis apparatus comprising:

an ultrasonic probe for transmitting an ultrasonic pulse beam toward a moving medium in a living body at a predetermined time interval $\Delta t$ defining a constant recurrence frequency and for receiving a reflected signal from a portion of the moving medium at any given depth in the living body;

converting means for mixing the received signal with a set of complex reference signals having a frequency n times (n: an integer) as high as the recurrence frequency of the transmitted ultrasonic beam and having a complex relation therebetween, thereby converting the received signal into complex signals including a sine component signal and a cosine component signal;

first operating means for computing the intensity of the ultrasonic wave reflected from the portion of the moving medium at said given depth in the living body on the basis of said complex signals, said first operating means using values a and b of said sine component signal at time t and time $(t+\Delta t)$ and values c and d of said cosine component signal at said times t and $(t+\Delta t)$ to compute the reflected signal intensity $l_t$ at said time t represented by $$l_t = (a^2 + c^2)^{\frac{1}{2}}$$

and the reflected signal intensity $l_{(t+\Delta t)}$ at said time $(t+\Delta t)$ represented by $$l_{(t+\Delta t)} = (b^2 + d^2)^{\frac{1}{2}},$$

second operating means for computing the moving speed of the moving medium at said given depth in the living body, said second operating means using said values a, b, c and d and the computed values of said reflected ultrasonic wave intensities $l_t$ and $l_{(t+\Delta t)}$ to compute angular displacements $\theta$ and $\delta$ represented by $$\theta = \frac{a}{\sin^{-1} l_t}$$

and $$\delta = \frac{b}{\sin^{-1} l_{(t+\Delta t)}},$$

and using the computed values of angular displacements $\theta$ and $\delta$ and the value of said predetermined time interval $\Delta t$ to compute a Doppler shift frequency $f_d$ represented by $$f_d = 2\pi \cdot (\delta - \theta)\Delta t,$$

the moving speed of the moving medium at said given depth in the living body being determined from the computed value of Doppler shift frequency $f_d$;

third operating means for computing the dispersion $\sigma$ of the moving speed computed by said second operating means when said moving medium is a fluid in the living body, said moving speed dispersion $\sigma$ being defined by $$\sigma = \sqrt{\frac{1}{n} \sum_{i=1}^{n} (v_i - \overline{N})^2}$$

$v_i$ being the values of the moving speed at said given depth in the living body computed by said first operating means and $\overline{N}$ being an average speed determined by $$\overline{N} = \frac{1}{n} \sum_{i=1}^{n} vi,$$

n being an integer;

operation selecting means associated with said third operating means for selecting whether the computation of the moving speed by said second operating means is to be executed or both the computation of the moving speed by said second operation means and the moving speed dispersion by said third operating means are to be executed; and display means for displaying, by a color change, at least one of the moving speed computed by said first operating means, and the correlation between the moving speed and the moving speed dispersion computed by said third operating means while displaying the reflected ultrasonic wave intensity by a luminance change.

3. An ultrasonic diagnosis apparatus comprising:

an ultrasonic probe for transmitting an ultrasonic pulse beam toward a moving medium in a living body at a constant recurrence frequency and for receiving a reflected signal from a portion of the moving medium at any given depth in the living body;

converting means for mixing the reflected signal with a set of complex reference signals having a frequency n times (n: an integer) as high as the recurrence frequency of the transmitted ultrasonic pulse beam and having a complex relation therebetween, thereby converting the received signal into complex signals;

a reflected signal intensity operating circuit for receiving said complex signals to determine the intensity of the signal reflected from the portion of the moving medium at said given depth in the living body;

a speed operating circuit for receiving said complex signals to determine the moving speed of the moving medium at said given depth in the living body;

a color encoder including a first circuit section for receiving data of the moving speed determined by said operating circuit to produce color data indicative of the respective amounts of first, second and third color components of first, second and third primary colors, respectively, at least two of said amounts depending on a value of the moving speed, and including a second circuit section for receiving said color data from said first circuit section and data of the reflected signal intensity determined by said reflected signal intensity operating circuit to add data of luminance, which changes depending on the value of the reflected signal intensity, to said color data, thereby producing a display data output including said color data to which the luminance data is added; and a display unit for receiving said display data output from said second circuit section of said color encoder to display a color determined by the mixture of said first to third primary colors based on the amounts of said first, second and third color components indicated by said color data while changing the luminance of said color in accordance with said luminance data, whereby the moving speed and the reflected signal intensity are displayed such that said color being displayed is changed depending on the value of the moving speed and the luminance of said color being displayed is changed depending on the value of the reflected signal intensity;

further comprising a speed dispersion operating circuit for receiving data of the moving speed determined by said speed operating circuit when said moving medium is a fluid in the living body to determine the dispersion of the moving speed from an average speed, and operation selecting means associated with said speed dispersion operating circuit for selecting whether the determination of the moving speed by said speed operating circuit is to be executed or both the determination of the moving speed by said speed operating circuit and the determination of the moving speed dispersion by said speed dispersion operating circuit are to be executed, and wherein said first circuit section of said color encoder further receives data of the moving speed dispersion determined by said speed dispersion operating circuit so that at least one of said amounts of said first, second and third color components indicated by said color data changes depending on a value of the moving speed dispersion, whereby the moving speed, the moving speed dispersion and the reflected signal intensity are displayed in a form in which said color being displayed by said display unit is changed depending on both the value of the moving speed and the moving speed dispersion while the luminance of said color being displayed is changed depending on the value of the reflected signal intensity.

4. An ultrasonic diagnoisis apparatus according to claim 3, wherein said first, second and third primary colors are red, green and blue, and the amounts of the red and blue components change depending on the value of the moving speed.

5. An ultrasonic diagnosis apparatus according to claim 3, wherein said first, second and third primary colors are red, green and blue, and the amounts of the red and blue components change depending on the value of the moving speed while the amount of green component changes depending on the value of the moving speed deviation.

* * * * *